(12) United States Patent
Toriyama

(10) Patent No.: US 9,986,891 B2
(45) Date of Patent: Jun. 5, 2018

(54) MEASUREMENT PROBE AND OPTICAL MEASUREMENT SYSTEM

(71) Applicant: OLYMPUS CORPORATION, Hachioji-shi, Tokyo (JP)

(72) Inventor: Seiki Toriyama, Hino (JP)

(73) Assignee: OLYMPUS CORPORATION, Tokyo (JP)

(*) Notice: Subject to any disclaimer, the term of this patent is extended or adjusted under 35 U.S.C. 154(b) by 134 days.

(21) Appl. No.: 15/266,406

(22) Filed: Sep. 15, 2016

(65) Prior Publication Data
US 2017/0082534 A1    Mar. 23, 2017

Related U.S. Application Data

(60) Provisional application No. 62/219,979, filed on Sep. 17, 2015.

(51) Int. Cl.
| | |
|---|---|
| *G01N 21/47* | (2006.01) |
| *A61B 1/00* | (2006.01) |
| *A61B 1/07* | (2006.01) |
| *A61B 5/00* | (2006.01) |
| *A61B 5/053* | (2006.01) |
| *G01N 21/49* | (2006.01) |
| *A61B 5/01* | (2006.01) |

(52) U.S. Cl.
CPC ...... *A61B 1/00039* (2013.01); *A61B 1/00096* (2013.01); *A61B 1/07* (2013.01); *A61B 5/0084* (2013.01); *A61B 5/0538* (2013.01); *A61B 5/6886* (2013.01); *A61B 5/01* (2013.01); *A61B 5/4238* (2013.01); *A61B 5/4255* (2013.01); *G01N 21/49* (2013.01); *G01N 2201/08* (2013.01)

(58) Field of Classification Search
CPC .... A61B 1/00039; G01N 21/49; G01N 21/47; G01N 2201/08
USPC ..................................................... 250/227.11
See application file for complete search history.

(56) References Cited

U.S. PATENT DOCUMENTS

| | | | |
|---|---|---|---|
| 8,743,362 B2 | 6/2014 | Gono | |
| 2003/0133112 A1* | 7/2003 | Tsutsui | G01N 21/474 356/338 |
| 2012/0302892 A1* | 11/2012 | Lue | A61B 5/0071 600/476 |

FOREIGN PATENT DOCUMENTS

| | | |
|---|---|---|
| JP | 5049415 B2 | 10/2012 |
| JP | 5101366 B2 | 12/2012 |
| JP | 5243719 B2 | 7/2013 |

* cited by examiner

*Primary Examiner* — Seung C Sohn
(74) *Attorney, Agent, or Firm* — Oliff PLC

(57) ABSTRACT

A measurement probe includes: a plurality of optical fibers including an illumination fiber configured to propagate light to irradiate a measuring object and including a light receiving fiber configured to receive scattered light retuned from the measuring object; and a detection portion configured to detect contact with the measuring object, the detection portion having a contact part provided on a part of a side portion of the measurement probe, the side portion forming a surface along a longitudinal direction of the measurement probe, the contact part being configured to be in contact with measuring object.

9 Claims, 12 Drawing Sheets

MEASUREMENT PROBE AND OPTICAL MEASUREMENT SYSTEM

CROSS-REFERENCE TO RELATED APPLICATIONS

This application is based upon and claims the benefit of priority from U.S. Provisional Patent Application No. 62/219,979, filed on Sep. 17, 2015, the entire contents of which are incorporated herein by reference.

BACKGROUND

1. Technical Field

The disclosure relates to a measurement probe and an optical measurement system for measuring optical characteristics of living tissue.

2. Related Art

In recent years, there has been known an optical measurement apparatus that irradiates living tissue with illumination light and estimates characteristics of living tissue based on a measuring value of detected light reflected or scattered from the living tissue., The optical measurement apparatus is used in combination with an endoscope for observing an internal organ such as a digestive organ. As such optical measurement apparatus, there has been proposed an optical measurement apparatus using low-coherence enhanced backscattering (LEBS) that detects characteristics of living tissue by irradiating the living tissue with a low-coherent white light having a short spatial coherence length from an illumination fiber of the measurement probe, by detecting scattered light entering from an angle different from each other using a plurality of light receiving fibers, and by measuring intensity distribution of the scattered light using a spectroscope provided for each of the light receiving fibers (see Japanese Patent No. 5049415, for example).

SUMMARY

In some embodiments, a measurement probe includes: a plurality of optical fibers including an illumination fiber configured to propagate light to irradiate a measuring object and including a light receiving fiber configured to receive scattered light retuned from the measuring object; and a detection portion configured to detect contact with the measuring object, the detection portion having a contact part provided on a part of a side portion of the measurement probe, the side portion forming a surface along a longitudinal direction of the measurement probe, the contact part being configured to be in contact with measuring object.

In some embodiments, an optical measurement system includes: an optical measurement apparatus configured to perform an optical measurement on a measuring object to measure characteristics of the measuring object; and a measurement probe having a plurality of optical fibers including an illumination fiber configured to propagate light to irradiate the measuring object and including a light receiving fiber configured to receive scattered light returned from the measuring object. The measurement probe includes a detection portion configured to detect contact with the measuring object, the detection portion having a contact part provided on a part of a side portion of the measurement probe, the side portion forming a surface along a longitudinal direction of the measurement probe, the contact part being configured to be in contact with measuring object. The optical measurement apparatus includes a detecting unit configured to detect whether or not the side portion on a distal end side of the measurement probe is being covered with the measuring object based on a detection value detected by the detection portion.

The above and other features, advantages and technical and industrial significance of this invention will be better understood by reading the following detailed description of presently preferred embodiments of the invention, when considered in connection with the accompanying drawings.

DETAILED DESCRIPTION

Hereinafter, modes for carrying out the present invention (hereinafter, referred to as "embodiment(s)") will be described with reference to the drawings. The same reference signs are used to designate the same elements throughout the drawings. The drawings are schematic, and a relationship between a thickness and a width of each member as well as a ratio and the like between the members may be different from actualities. Furthermore, between the drawings, there may be a part for which a dimensional relationship or a ratio is different from each other. Nate also that the present invention is not to be limited by the embodiments.

First Embodiment

Figure 1:
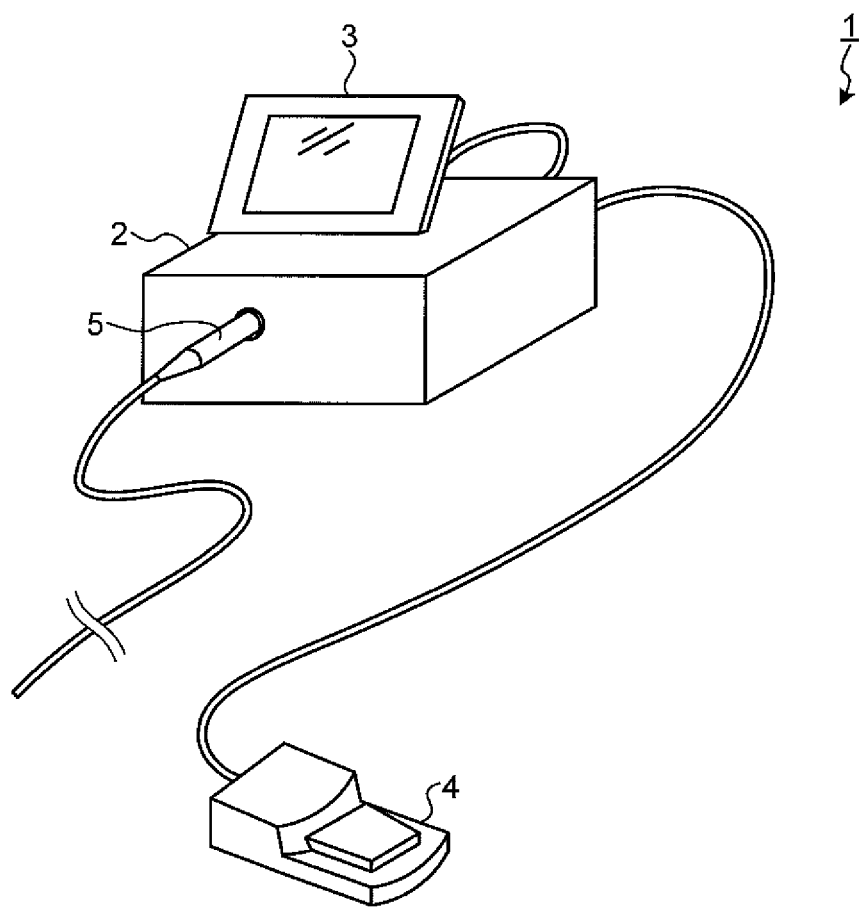
FIG. 1 is an external view illustrating a configuration of an optical measurement system according to a first embodiment of the present invention.
Figure 2:
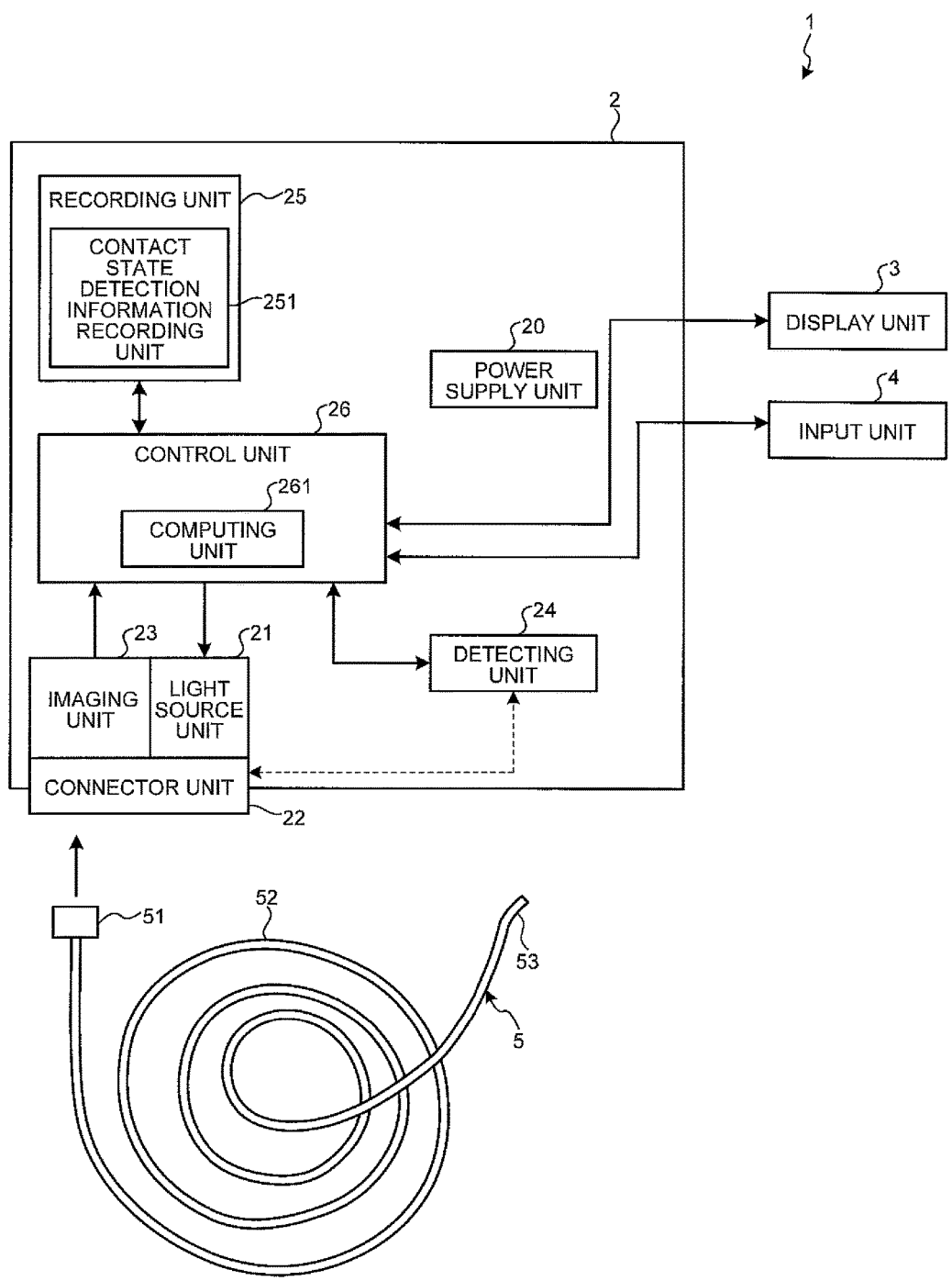
FIG. 2 is a block diagram schematically illustrating a functional configuration of the optical measurement system according to the first embodiment of the present invention.

FIG. 1 is an external view illustrating a configuration of an optical measurement system 1 according to a first embodiment of the present invention. FIG. 2 is a black diagram schematically illustrating a functional configuration of the optical measurement system 1 according to the first embodiment of the present invention.

The optical measurement system 1 illustrated in FIGS. 1 and 2 includes: an optical measurement apparatus 2 that performs an optical measurement on a measuring object such as living tissue, which is a scatterer, and detects characteristics (properties) of the measuring object; a display unit 3 that displays a measurement result of the optical measurement apparatus 2; an input unit 4 that receives input of an instruction signal that instructs the optical measurement apparatus 2 to perform the measurement; and an elongated measurement probe 5 that is attachable to and detachable from the optical measurement apparatus 2 and is configured to be inserted into a subject.

First, a configuration of the optical measurement apparatus 2 will be described. The optical measurement apparatus 2 includes a power supply unit 20, a light source unit 21, a connector unit 22, an imaging unit 23, a detecting unit 24, a recording unit 25, and a control unit 26. The power supply unit 20 supplies electric power to each of the units of the optical measurement apparatus 2.

The light source unit 21 emits illumination light to the measurement probe 5 through the connector unit 22. The light source unit 21, for example, is implemented by using a light emitting element that is an incoherent light source such as a white light emitting diode (LED), one or more lenses that collect light emitted by the light emitting element, and a filter that transmits light of a predetermined wavelength band. As such lens, for example, a condenser lens, a collimator lens, and the like may be listed. In the first embodiment, the light source unit 21 emits the illumination light containing light of a component with a large numerical aperture (NA). The light source unit 21 emits incoherent light having at least one spectrum component, as the illumination light, to the measurement probe 5 through the connector unit 22. The light emitting element may also be implemented by using the incoherent light source such as a Xenon lamp, a tungsten lamp, and a halogen lamp. Furthermore, one or a plurality of condenser lenses is provided as necessary.

The connector unit 22 is configured to connect the measurement probe 5 to the optical measurement apparatus 2 in a detachable manner.

The imaging unit 23 receives return light of the illumination light that has been emitted from a distal end of the measurement probe 5 and has been reflected and/or scattered from the measuring object, performs photoelectric conversion on the received light to generate an electric signal, and outputs the electric signal to the control unit 26. The imaging unit 23 is implemented by using an image sensor such as a charge coupled device (CCD) image sensor or a complementary metal oxide semiconductor (CMOS) image sensor, or a sensor such as a photo diode (PD).

The detecting unit 24 is electrically connectable to the measurement probe 5, and it detects a detection value (e.g. electrical current value) through the measurement probe 5. Based on the detected detection value, the detecting unit 24 detects whether or not the distal end of the measurement probe 5 is sunk into the measuring object.

The recording unit 25 records various programs for operating the optical measurement apparatus 2 as well as various data and various parameters used by the optical measurement apparatus 2. The recording unit 25 is implemented by using a volatile memory, a non-volatile memory, or the like. The recording unit 25 temporarily records information and data that are being processed by the optical measurement apparatus 2. Furthermore, the recording unit 25 records a measurement result of the optical measurement apparatus 2 and arrangement information according to arrangement of a light receiving fiber. The recording unit 25 may also be constituted by a removable memory card.

The recording unit 25 has a contact state detection information recording unit 251 that stores information for detecting a contact state between the measurement probe 5 and the living tissue, which is the measuring object. The contact state detection information recording unit 251 is specifically a threshold for determining the contact state, and it stores the threshold for determining whether or not the contact state is in an ideal condition.

The control unit 26 controls processing operation of each of the units of the optical measurement apparatus 2. The control unit 26 is constituted by using a central processing unit (CPU) and the like. By performing forwarding and the like of instruction information and data to each of the units of the optical measurement apparatus 2, the control unit 26 totally controls the optical measurement apparatus 2. The control unit 26 has a computing unit 261.

Based on the electric signal input from the imaging unit 23 (e.g. a signal corresponding to a measured light amount), the computing unit 261 performs a plurality of arithmetic processing and calculates a characteristic value related to characteristics of the measuring object.

The display unit 3 outputs various information on the optical measurement apparatus 2. Specifically, the display unit 3 displays information input from the optical measurement apparatus 2. The display unit 3 is implemented by using a display panel such as of liquid crystal or organic electro luminescence (EL), a speaker, and the like. Note that it is also possible to provide, on a display screen of the display unit 3, a touch panel that receives input of a position signal corresponding to a contact position from outside.

The input unit 4 receives input of the instruction signal instructing the optical measurement apparatus 2 to perform measurement. The input unit 4 is implemented by using, for example, an input interface such as a foot switch, a keyboard, and a mouse.

The measurement probe 5 is constituted by using at least a plurality of optical fibers. Specifically, the measurement probe 5 is implemented by using an illumination fiber (illuminating channel) that irradiates the measuring object with the illumination light, and a plurality of light receiving fibers (light-receiving channel) in which the return light of the illumination light reflected and/or scattered from the measuring object enters at different angles. The measurement probe 5 includes: a proximal end portion 51 configured to be connected to the connector unit 22 of the optical measurement apparatus 2 in a detachable manner; a flexible portion 52 having flexibility; and a distal end portion 53 that emits the illumination light supplied from the light source unit 21 through the connector unit 22 and receives the return light of the illumination light from the measuring object.

Figure 3:
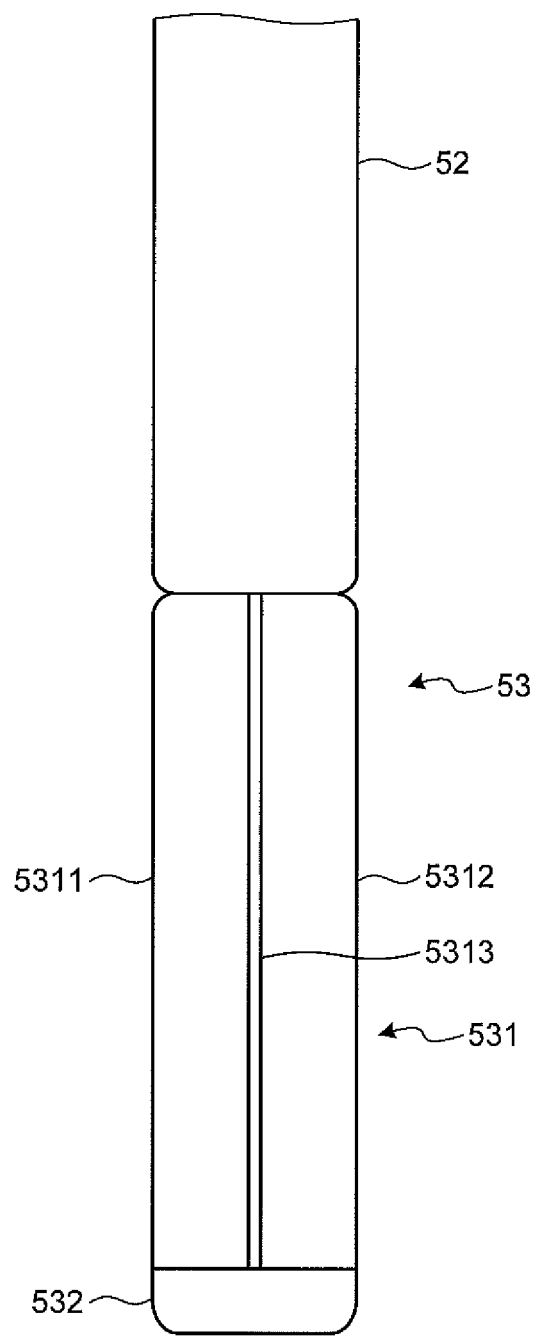
FIG. 3 is a side view schematically illustrating a configuration of a distal end portion of a measurement probe according to the first embodiment of the present invention.
Figure 4:
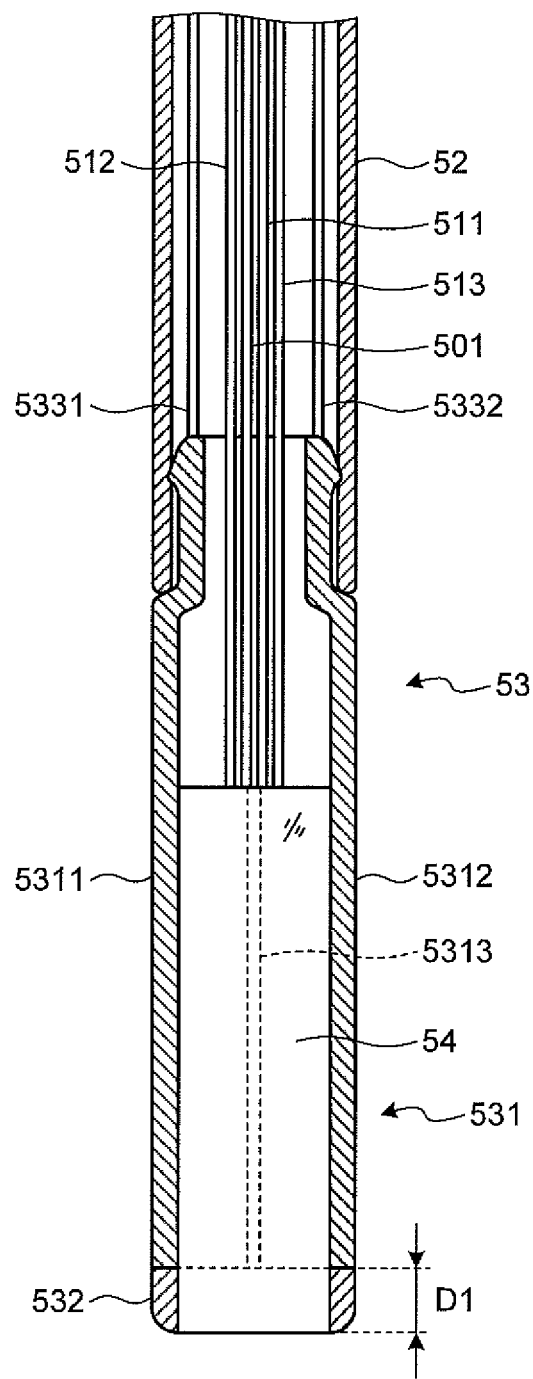
FIG. 4 is a partial sectional view schematically illustrating a configuration of a distal end portion of the measurement probe according to the first embodiment of the present invention.

Here, a configuration of the distal end portion 53 of the measurement probe 5 will be described. FIG. 3 is a side view schematically illustrating the configuration of the distal end portion of the measurement probe according to the first embodiment of the present invention. FIG. 4 is a partial sectional view schematically illustrating the configuration of the distal end portion of the measurement probe according to the first embodiment of the present invention. Note that the partial sectional view in FIG. 4 illustrates a section, which is a cutting plane along a central axis of the measurement probe 5, parallel to the central axis.

The measurement probe 5 includes an illumination fiber 501 that transmits the illumination light supplied from the light source unit 21 through the connector unit 22 to the distal end portion 53 of the measurement probe 5 and irradiates the measuring object with the illumination light, and a first light receiving fiber 511, a second light receiving fiber 512, and a third light receiving fiber 513 in which the return light of the illumination light reflected and/or scattered from the measuring object enters at a different angle from each other from the distal end portion 53 and is transmitted to the proximal end portion 51. In the first embodiment, three light receiving fibers are provided; however, the number of the light receiving fibers is not limited to three, and a design change will be made as necessary.

At the distal end of the distal end portion 53, a rod lens 54 is provided as an optical member that is connected to the illumination fiber 501 and the light receiving fibers (the first light receiving fiber 511, the second light receiving fiber 512, and the third light receiving fiber 513) at one end thereof, and that maintains a distance between the measuring object and the illumination and light receiving fibers constant.

In the measurement probe 5, the illumination fiber 501, the first light receiving fiber 511, the second light receiving fiber 512, and the third light receiving fiber 513 abut on the rod lens 54. Therefore, the distance from the illumination fiber 501, the first light receiving fiber 511, the second light receiving fiber 512, and the third light receiving fiber 513 to the measuring object is maintained to be a length of the rod lens 54 in a longitudinal direction of the measurement probe 5.

The distal end portion 53 includes: a tubular holding portion 531 which is connected to the flexible portion 52 and into which the illumination fiber 501, the first light receiving fiber 511, the second light receiving fiber 512, and the third light receiving fiber 513 are inserted, and which holds a part of the rod lens 54; and a hollow cylindrical insulating portion 532 formed of insulating material, attached to an end portion on a different side of a side connecting to the flexible portion 52 of the holding portion 531, and attached to a distal end of the rod lens 54. The holding portion 531 may be attached to the flexible portion 52 by pressing and fitting the holding portion 531 against and into the flexible portion 52 or by a well-known adhesion means (with an adhesive and the like) or a fixing means (fitting, screwing, and the like).

The holding portion 531 includes: a first member 5311 constituted by using a conductive material, extending along the longitudinal direction of the measurement probe 5, and having an arch-shaped section, which is a cutting plane of a plane orthogonal to the longitudinal direction thereof; a second member 5312 arranged symmetric to the first member 5311 relative to a plane parallel to the longitudinal direction of the measurement probe 5, formed of conductive material, extending along the longitudinal direction of the measurement probe 5, and having an arch-shaped section, which is the cutting plane of the plane orthogonal to the longitudinal direction; and two third members 5313 that are formed of insulating material and connect the first member 5311 to the second member 5312. The first member 5311, the second member 5312, and the third members 5313 constitute a cylindrical-shaped holding portion 531 by coupling the first member 5311 to the second member 5312 by the third members 5313.

To the first member 5311, a wire 5331 is connected at an end portion thereof on a side connecting to the flexible portion 52. In the same way, to the second member 5312, a wire 5332 is connected at the end portion thereof on the side connecting to the flexible portion 52. Each of the wires 5331 and 5332 is electrically connected to the detecting unit 24, and a very weak voltage is applied thereto. For this reason, when a conductive medium is interposed between the first member 5311 and the second member 5312, a circuit is formed by the first member 5311, the second member 5312, the wires 5331 and 5332, and the detecting unit 24, and thus, a weak electrical current flows. That is, the first member 5311 and the second member 5312 function as a pair of electrodes (contact part) in the circuit. The first member 5311, the second member 5312, the third members 5313, and the wires 5331 and 5332 constitute a detection portion.

The insulating portion 532 has an end portion that is configured to be in contact with the measuring object and that is located on a plane which is the same as a distal end surface of the rod lens 54. An arrangement distance of the insulating portion 532 in the longitudinal direction of the measurement probe 5 (a distance D1 illustrated in FIG. 4) may be long enough to detect sinking of the measurement probe 5 into the measuring object, and the distance is set, for example, at about several millimeters. As long as the sinking is detectable, the insulating portion 532 may be provided on a side portion including an end portion side where the measurement probe 5 is in contact with the measuring object. In this case, the distance D1 is zero.

Figure 5:
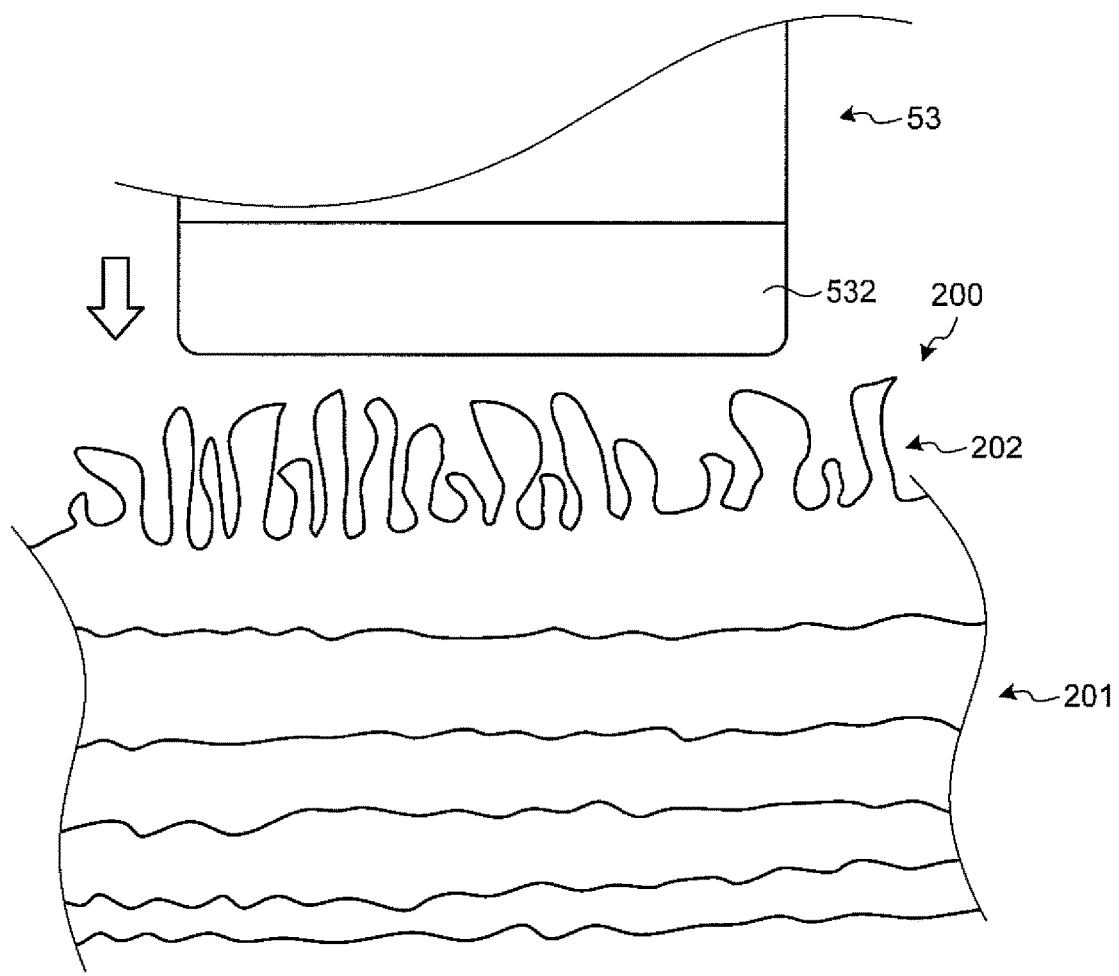
FIG. 5 is an illustrative diagram showing contact between the distal end portion of the measurement probe according to the first embodiment of the present invention and living tissue.

Next, contact between the measurement probe 5 and the living tissue, which is the measuring object, will be described with reference to FIGS. 5 to 8. FIG. 5 is an illustrative diagram showing the contact between the distal end portion of the measurement probe and the living tissue according to the first embodiment of the present invention. In this first embodiment, the living tissue, which is the measuring object, will be described to be a mucosa; however, it may also be another tissue. As illustrated in FIG. 5, living tissue 200, which is the measuring object, has a submucosal layer 201, and a villus 202 constituting a tissue surface of the living tissue 200. During measurement using the measurement probe 5, the distal end of the measurement probe 5 is contacted to a surface of the living tissue 200. The illumination fiber 501 irradiates the living tissue 200 with the illumination light through the rod lens 54, and the first light receiving fiber 511, the second light receiving fiber 512, and the third light receiving fiber 513 receive the return light of the illumination light reflected and/or scattered from the living tissue 200 through the rod lens 54.

Figure 6:
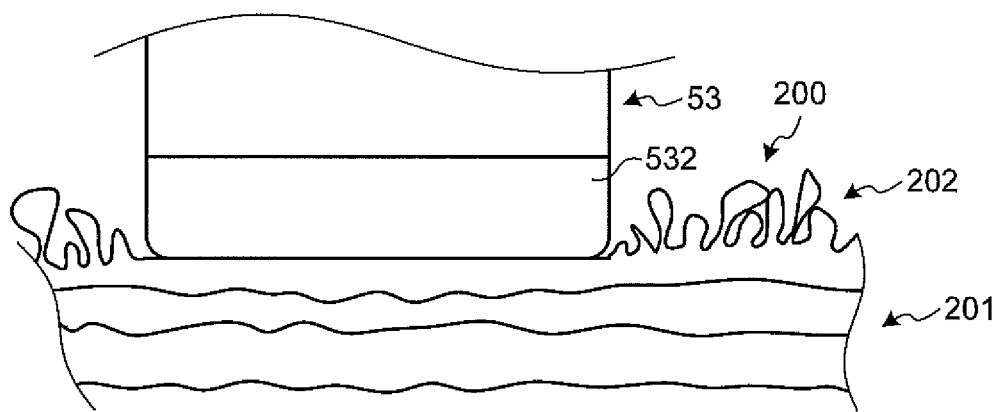
FIG. 6 is an illustrative diagram showing an ideal contact state between the distal end portion of the measurement probe according to the first embodiment of the present invention and the living tissue.
Figure 7:
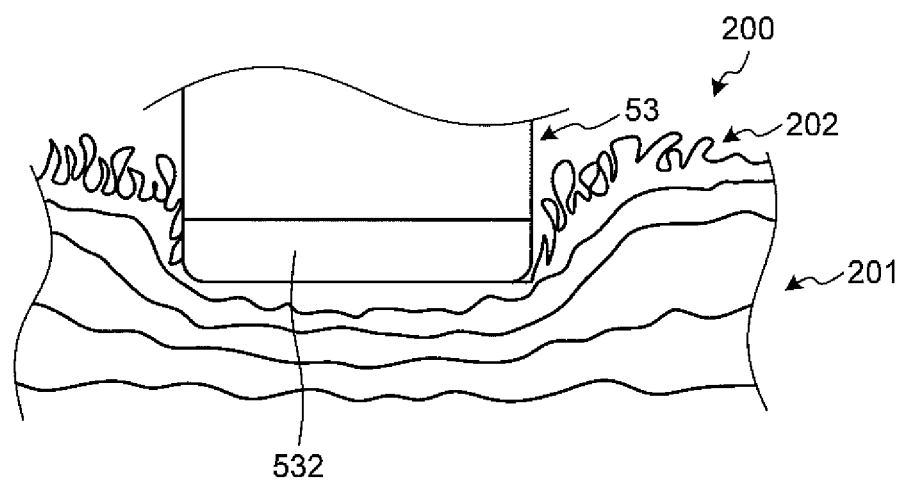
FIG. 7 is an illustrative diagram showing a non-ideal contact state between the distal end portion of the measurement probe according to the first embodiment of the present invention and the living tissue.

FIG. 6 is an illustrative diagram showing an ideal contact state between the distal end portion of the measurement probe and the living tissue according to the first embodiment of the present invention. FIG. 7 is an illustrative diagram showing a non-ideal contact state between the distal end portion of the measurement probe and the living tissue according to the first embodiment of the present invention. When the measurement probe 5 and the living tissue 200 are in the ideal contact state, a distal end of the insulating portion 532 and a distal end surface of the rod lens 54 are pressed against the villus 202, whereby the villus 202 is in a crushed condition. At this time, no load from the measurement probe 5 is applied to the submucosal layer 201, whereby the submucosal layer 201 is not deformed (see FIG. 6).

In contrast, in the non-ideal contact state between the measurement probe 5 and the living tissue 200, for example, a distal end surface of the rod lens 54 is pressed against the villus 202, and the submucosal layer 201 and the villus 202 are crushed, whereby the distal end of the measurement probe 5 including the insulating portion 532 is being sunk into the living tissue 200. In the non-ideal contact state, the load from the measurement probe 5 is applied also to the submucosal layer 201, the submucosal layer 201 is deformed, and a part of the holding portion 531 is being covered with the living tissue 200 (see FIG. 7). In this case, the first member 5311 and the second member 5312 are in contact with the mucosa of the living tissue 200, the villus 202, and the like on the distal end side, whereby an electric circuit is formed by the first member 5311, the second member 5312, the wires 5331 and 5332, and the detecting unit 24, whereby it is electrically conductive.

Figure 8:
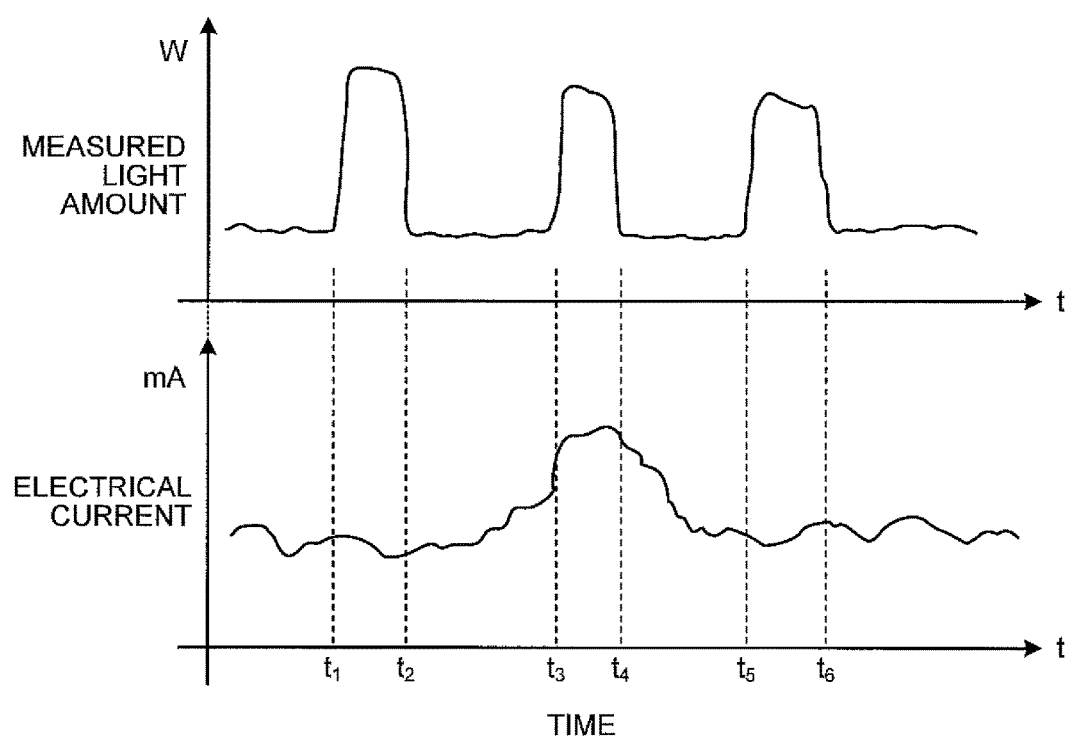
FIG. 8 is a graphical illustration of the contact between the distal end portion of the measurement probe according to the first embodiment of the present invention and the living tissue, which is a graph showing a temporal change of a measured light amount and an electrical current value.

FIG. 8 is a graphical illustration of the contact between the distal end portion of the measurement probe and the living tissue according to the first embodiment of the present invention, which is a graph showing a time (t) change of a measured light amount (W) and an electrical current value (mA). FIG. 8 provides an example of performing a measurement three times in total between a time $t_1$ and a time $t_2$, between a time $t_3$ and a time $t_4$, and between a time $t_5$ and a time $t_6$. Hereinafter, the measurement performed between the time $t_1$ and the time $t_2$ is referred to as a first measurement, the measurement performed between the time $t_3$ and the time $t_4$ is referred to as a second measurement, and the measurement performed between the time $t_5$ and the time $t_6$ is referred to as a third measurement.

In the first and third measurements, the measured light amount increases while an amount of change of the electrical current value is small. In a case where the measurement is performed in the ideal contact state between the measurement probe 5 and the living tissue 200, the first member 5311 and the second member 5312 are not in contact with the mucosa, the villus 202, and the like of the living tissue 200, whereby the electric circuit constituted of the first member 5311, the second member 5312, the wires 5331 and 5332, and the detecting unit 24 is not formed. For this reason, a rate of change of the electrical current value hardly changes between before and after the measurement and during the measurement. Therefore, the first and third measurements are regarded as being measured in the ideal contact state between the measurement probe 5 and the living tissue 200.

In contrast, in the second measurement, the measured light amount increases while the amount of change of the electrical current value is large. In a case where the measurement is performed in the non-ideal contact state between the measurement probe 5 and the living tissue 200, the first member 5311 and the second member 5312 are in contact with the mucosa of the living tissue 200 and the villus 202 at a distal end side thereof, whereby the electric circuit constituted of the first member 5311, the second member 5312, the wires 5331 and 5332, and the detecting unit 24 is formed. For this reason, the rate of change of the electrical current value is larger during the measurement than before and after the measurement. In this way, the second measurement, in which the amount of change of the electrical current value is large during the measurement, may be regarded as being measured in the non-ideal contact state between the measurement probe 5 and the living tissue 200.

As described above, in the ideal contact state between the measurement probe 5 and the living tissue 200, a change of the detection value (electrical current value) detected through the distal end portion 53 is small, and in the non-ideal contact state between the measurement probe 5 and the living tissue 200, the change of the detection value (electrical current value) detected through the distal end portion 53 is large. By comparing this change of the electrical current value with a threshold, the detecting unit 24 determines the contact state between the measurement probe 5 and the living tissue 200. Specifically, the detecting unit 24 compares the detection value with the threshold, for example, by using any of a maximum value, a minimum value, an average value, and a most frequent value of the electrical current value detected between the time $t_1$ and the time $t_2$ in the first measurement as the detection value. In a case where the detection value is larger than the threshold, it is determined that the first measurement is performed in the non-ideal contact state between the measurement probe 5 and the living tissue 200. That is, by determining whether or not the measurement probe 5 is sunk in the living tissue 200, the detecting unit 24 detects whether or not the measurement is performed in the non-ideal contact state between the distal end of the measurement probe 5 and the living tissue 200. In the same way, the detecting unit 24 determines the contact state based on the detection value detected during each period of the measurements.

According to a detection result by the detecting unit 24, it is also possible to allow the control unit 26 to add information related to the contact state to the characteristic value related to the characteristics of the measuring object, or to allow the control unit 26 to display the information related to the contact state that is detected on the display unit 3. Light or sound may be used to notify that the contact state is non-ideal. If light is used, a notifying unit may be realized by using a LED, and if sound is used, the notifying unit may be realized by using a buzzer and the like. Accordingly, it is possible to grasp whether or not the measurement has been performed in the ideal contact state, that is, in the contact state in which a highly-reliable measurement result may be obtained or in the non-ideal contact state.

Figure 9:
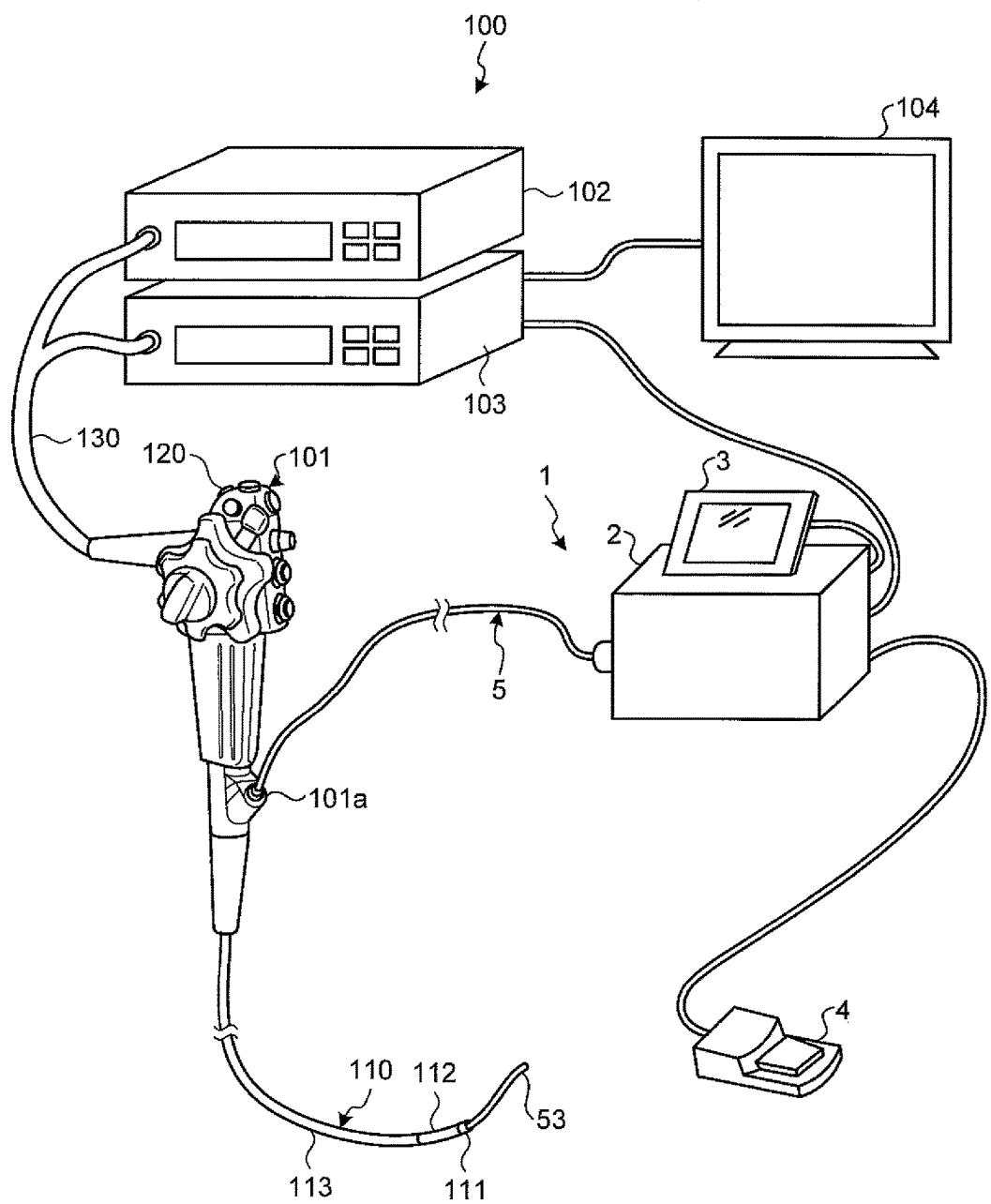
FIG. 9 is a schematic view illustrating a situation in which the optical measurement system is used in an endoscope system according to the first embodiment of the present invention.

As illustrated in FIG. 9, by inserting the measurement probe 5 through a processing tool channel 101a provided on an endoscope 101 (endoscope) of an endoscope system 100, the optical measurement system 1 configured as described above may be used together with the endoscope 101.

The endoscope system 100 includes: the endoscope 101 configured to capture an in-vivo image of the subject by inserting the distal end portion thereof into the subject; a light source device 102 configured to generate the illumination light to be emitted from a distal end of the endoscope 101; a processing device 103 configured to perform predetermined image processing on the in-vivo image captured by the endoscope 101 as well as totally control overall operation of the endoscope system 100; and a display device 104 configured to display the in-vivo image on which the image processing has been performed by the processing device 103.

The endoscope 101 includes: an thin elongated shape insertion unit 110 having flexibility; an operating unit 120 connected to a proximal end side of the insertion unit 110 and receiving input of various operation signals; and a universal code 130 that extends in a direction different from a direction in which the insertion unit 110 extends from the operating unit 120 and incorporates various cables to be connected to the light source device 102 and the processing device 103.

The insertion unit 110 includes: a distal end portion 111 having therein an image sensor having pixels arranged two-dimensionally, each pixel being configured to receive light and perform photoelectric conversion on the received light to generate a signal; and a bendable portion 112 having a plurality of bending pieces; and a long-shaped flexible tube portion 113 connected to a proximal end side of the bendable portion 112 and having flexibility.

In the measurement probe 5, which is inserted into the endoscope 101 and is inserted inside a subject, the illumination fiber 501 irradiates the measuring object with the illumination light, each of the first light receiving fiber 511, the second light receiving fiber 512, and the third light receiving fiber 513 receives the return light of the illumination light reflected and/or scattered from the measuring object through the rod lens 54 at the distal end portion 53, and outputs the return light to a light-receiving surface of the imaging unit 23. Then, based on information received by the imaging unit 23, the computing unit 261 calculates the characteristic value of the characteristics of the measuring object. At the same time, based on the detection value detected through the distal end portion 53, the detecting unit 24 detects sinking of the measurement probe 5 into the measuring object. The control unit 26 outputs a detection result of the contact state between the measurement probe 5 and the living tissue by the detecting unit 24 together with a calculation result.

According to the above-described first embodiment of the present invention, at the distal end portion 53 of the measurement probe 5, the detection value is changed by interposing or not interposing a conductive medium between the first member 5311 and the second member 5312, which are provided at positions slightly apart from the distal end side where the measurement probe 5 is in contact with the measuring object, whereby by using characteristics of the detection value that is different between when the measurement probe 5 is sunk into the measuring object and when the measurement probe 5 is not sunk therein, detection of sinking into the measuring object becomes possible. Accordingly, it is possible to determine reliability of the measurement result that is obtained based on the detection result of presence or absence of the sinking, whereby it is possible to obtain an appropriate measurement result in the measurement performed by contacting the measurement probe with the living tissue.

Second Embodiment

Figure 10:
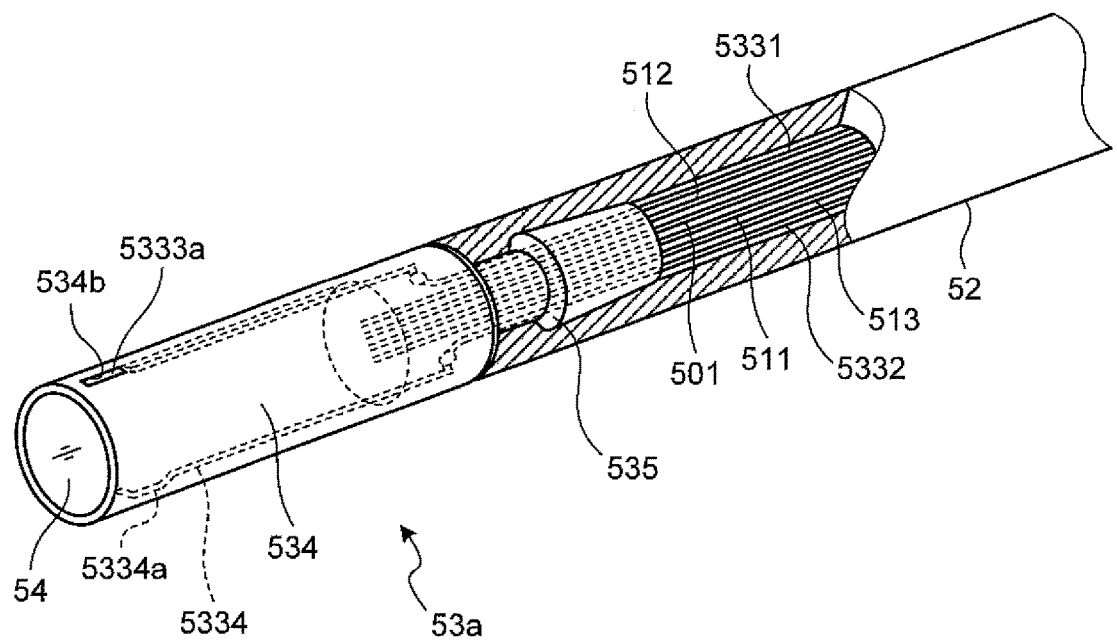
FIG. 10 is a perspective view schematically illustrating a configuration of a distal end portion of a measurement probe according to a second embodiment of the present invention.
Figure 11:
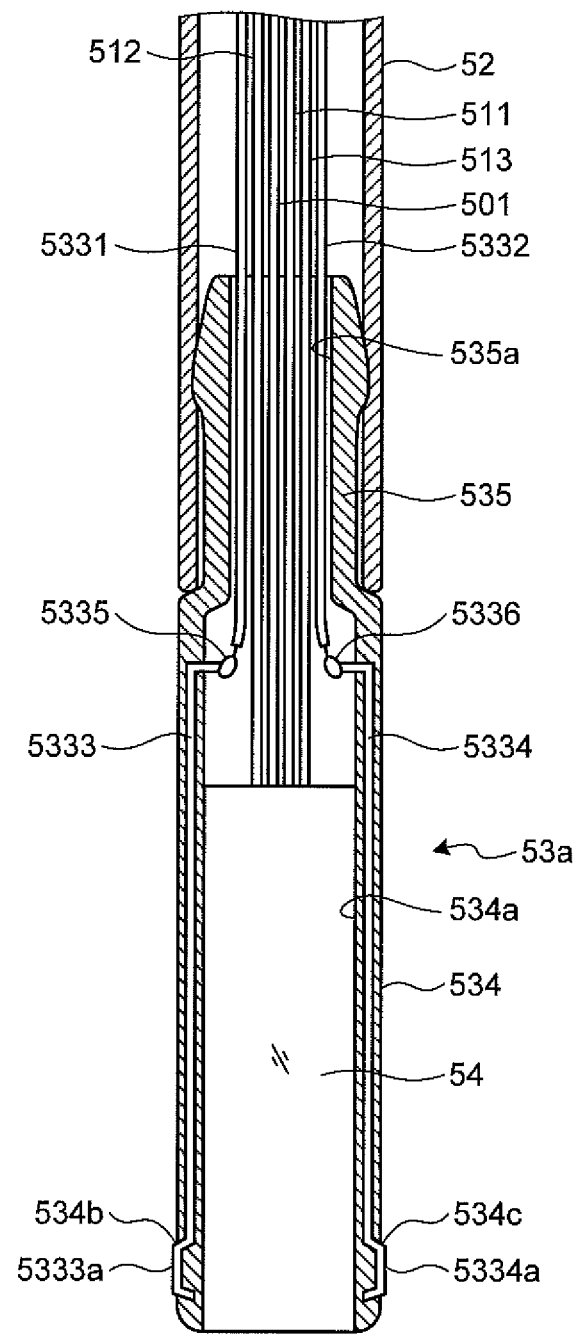
FIG. 11 is a partial sectional view schematically illustrating a configuration of the distal end portion of the measurement probe according to the second embodiment of the present invention.

FIG. 10 is a perspective view schematically illustrating a configuration of a distal end portion of a measurement probe according to a second embodiment of the present invention. FIG. 11 is a partial sectional view schematically illustrating the configuration of the distal end portion of the measurement probe according to the second embodiment of the present invention. The same reference signs are used to designate the same elements as those described above. In the above-described first embodiment, the holding portion 531 includes the conductive first member 5311 and the second member 5312, and sinking of the measurement probe 5 is detected based on the detection value detected through the first member 5311 and the second member 5312. In the second embodiment, however, a part of an electrode is exposed on a distal end side of a distal end portion 53a, and the sinking of the measurement probe 5 is detected based on the detection value detected through the exposed electrode.

The measurement probe 5 according to the second embodiment includes the above-described proximal end portion 51, the above-described flexible portion 52, and the distal end portion 53a configured to emit illumination light supplied from the light source unit 21 through the connector unit 22 and to receive return light of the illumination light from a measuring object.

The distal end portion 53a is formed of insulating material and is connected to the flexible portion 52 at one end thereof. A part of the illumination fiber 501, the first light receiving fiber 511, the second light receiving fiber 512, and the third light receiving fiber 513 is inserted into the distal end portion 53a. The distal end portion 53a holds the rod lens 54.

The distal end portion 53a includes: a tubular holding portion 534 that is formed of insulating material and holds at least the rod lens 54; and a tubular connecting portion 535 which is connected to the holding portion 534 at one end thereof and connected to the flexible portion 52 at the other end thereof, and into which the illumination fiber 501, the first light receiving fiber 511, the second light receiving fiber 512, and the third light receiving fiber 513 are inserted. The connecting portion 535 may be attached to the flexible portion 52 by pressing and fitting the connecting portion 535 against and into the flexible portion 52 or by a well-known adhesion means (with an adhesive and the like) or a well-known fixing means (fitting, screwing, and the like).

The holding portion 534 has a hole portion 534a, and window portions 534b and 534c. The hole portion 534a is a hole which holds the rod lens 54 and through which a part of the illumination fiber 501, the first light receiving fiber 511, the second light receiving fiber 512, and the third light receiving fiber 513 is inserted. The window portions 534b and 534c are holes provided at positions slightly apart from a distal end of the measurement probe 5 where the measurement probe 5 is in contact with the measuring object. The hole portion 534a communicates with outside through the window portions 534b and 534c. The window portions 534b and 534c are provided at positions slightly on a proximal end side from the distal end of the measurement probe 5, for example, at the position away from the distal end by the distance D1 illustrated in FIG. 4. As long as the sinking is detectable, the window portions 534b and 534c may be provided on a side portion including an end portion side where the measurement probe 5 is in contact with the measuring object.

Furthermore, as illustrated in FIG. 11, the holding portion 534 includes belt-shaped electrodes 5333 and 5334 along a longitudinal direction of the distal end portion 53a. The electrode 5333 has an exposed portion 5333a exposed to the outside through a window portion 534b. The electrode 5334 has an exposed portion 5334a exposed to the outside through a window portion 534c. As illustrated in FIG. 11, the electrodes 5333 and 5334 may be embedded inside the holding portion 534 by insert molding or may be arranged along a wall surface of the hole portion 534a.

At an end portion on a side of the connecting portion 535, the electrode 5333 is connected to a wire 5331 through a solder 5335. In the same way, at the end portion on the side of the connecting portion 535, the electrode 5334 is connected to a wire 5332 through a solder 5336. In the same way as the above-described first embodiment, each of the wires 5331 and 5332 is electrically connected to the detecting unit 24, and a very weak voltage is applied thereto. For this reason, when a conductive medium is interposed between the electrodes 5333 and 5334, a circuit is formed by the electrodes 5333 and 5334, the wires 5331 and 5332, and the detecting unit 24, and thus, a weak electrical current flows. That is, the electrodes 5333 and 5334 function as a pair of electrodes (detection portion) in the circuit. The exposed portions 5333a and 5334a function as contact parts to be in contact with the measuring object.

An outer peripheral surface of the connecting portion 535 has a stepped shape along the longitudinal direction of the distal end portion 53a. The connecting portion 535 has a hole portion 535a that is a hole into which a part of the illumination fiber 501, the first light receiving fiber 511, the second light receiving fiber 512, and the third light receiving fiber 513 is inserted.

In performing measurement by contacting the distal end portion 53e having the above-described configuration with the living tissue 200 (see FIG. 5 and the like), in the same way as the above-described first embodiment, in an ideal contact state between the measurement probe 5 and the living tissue 200, a change of the detection value (electrical current value) detected through the distal end portion 53a (electrodes 5333 and 5334) is small, and in a non-ideal contact state between the measurement probe 5 and the living tissue 200, the change of the detection value (electrical current value) detected through the distal end portion 53a is large. By comparing this change of the electrical current value with a threshold, the detecting unit 24 determines presence or absence of sinking of the measurement probe 5 into the living tissue 200 and detects whether or not the distal end of the measurement probe 5 is in the ideal contact state with the living tissue 200.

According to the above-described second embodiment of the present invention, at the distal end portion 53a of the measurement probe 5, the detection value is changed by interposing or not interposing a conductive medium between the electrodes 5333 and 5334, which are provided at positions slightly apart from the distal end side where the measurement probe 5 is in contact with the measuring object, whereby by using characteristics of the detection value that is different between when the measurement probe 5 is sunk into the measuring object and when the measurement probe 5 is not sunk therein, detection of sinking into the measuring object becomes possible. Accordingly, it is possible to determine reliability of a measurement result that is obtained based on a detection result of the presence or absence of the sinking, whereby it is possible to obtain an appropriate measurement result in the measurement performed by contacting the measurement probe with the living tissue.

Third Embodiment

Figure 12:
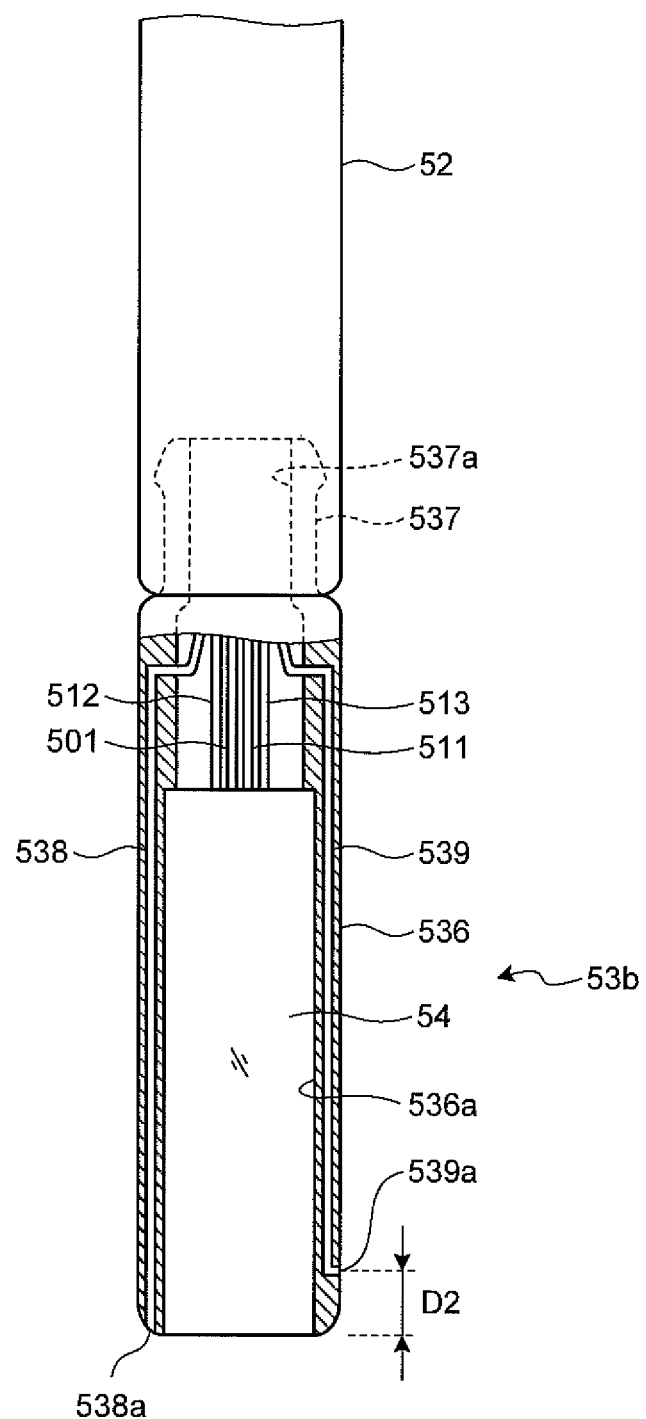
FIG. 12 is a partial sectional view schematically illustrating a configuration of a distal end portion of a measurement probe according to a third embodiment of the present invention.

FIG. 12 is a partial sectional view schematically illustrating a configuration of a distal end portion of a measurement probe according to a third embodiment of the present invention. The same reference signs are used to designate the same elements as those described above. In the above-described first and second embodiments, the sinking of the measurement probe 5 is detected based on the detection value of the electrical current value detected through the first member 5311 and the second member 5312 or through the electrodes 5333 and 5334; however, in the third embodiment, a thermocouple is exposed on a distal end side of a distal end portion 53b, and a thermoelectric current (temperature), which is detected through the exposed thermocouple, is detected. Based on the detected value, sinking of the measurement probe 5 is detected.

The measurement probe 5 according to the third embodiment includes the above-described proximal end portion 51, the flexible portion 52, and the distal end portion 53b configured to emit the illumination light supplied from the light source unit 21 through the connector unit 22 and to receive return light of the illumination light from a measuring object.

The distal end portion 53b is formed of insulating material and is connected to the flexible portion 52 at one end thereof. A part of the illumination fiber 501, the first light receiving fiber 511, the second light receiving fiber 512, and the third light receiving fiber 513 is inserted into the distal end portion 53b. The distal end portion 53b holds the rod lens 54.

The distal end portion 53b includes: a tubular holding portion 536 that is formed of insulating material and holds at least the rod lens 54; and a tubular connecting portion 537 which is connected to the holding portion 536 at one end thereof and connected to the flexible portion 52 at the other end thereof, and into which the illumination fiber 501, the first light receiving fiber 511, the second light receiving fiber 512, and the third light receiving fiber 513 are inserted. The connecting portion 537 may be attached to the flexible portion 52 by pressing and fitting the connecting portion 537 against and into the flexible portion 52 or by a well-known adhesion means (with an adhesive and the like) or by a well-known fixing means (fitting, screwing, and the like).

The holding portion 536 has a hole portion 536a that is a hole which holds the rod lens 54 and through which a part of the illumination fiber 501, the first light receiving fiber 511, the second light receiving fiber 512, and the third light receiving fiber 513 can be inserted.

The holding portion 536 has a first thermocouple 538 and a second thermocouple 539 that extend along a longitudinal direction of the distal end portion 53b. The first thermocouple 538 (second detection portion) has two different metallic members and two junctions connecting the metallic members to each other. One end portion of the first thermocouple 538 including one of the junctions is electrically connected to the detecting unit 24, and the other end portion of the first thermocouple 538 including the other junction (a distal end portion 538a illustrated in FIG. 12, i.e. second contact part) is exposed to the outside from an end face of the holding portion 536. The second thermocouple 539 (detection portion) has two different metallic members and two junctions connecting the metallic members to each other. One end portion of the second thermocouple 539 including one of the junctions is electrically connected to the detecting unit 24, and the other end portion of the second thermocouple 539 including the other junction (a distal end portion 539a illustrated in FIG. 12, i.e. contact part) is exposed to the outside from a side surface of the holding portion 536 at a position slightly apart from the end face of the holding portion 536. The distal end portion 539a of the second thermocouple 539 is provided at a position slightly toward a proximal end side from the distal end of the measurement probe 5 to be in contact with a measuring object, for example, at a position away from the distal end of the measurement probe 5 by a distance D2 illustrated in FIG. 12. The distance D2 may be long enough to detect sinking of the measurement probe 5 in the measuring object, whereby the distance may be set to about several millimeters, for example. As illustrated in FIG. 12, the first thermocouple 538 and the second thermocouple 539 may be embedded inside the holding portion 536 by insert molding or may be arranged along a wall surface of the hole portion 536a.

In the first thermocouple 538 and the second thermocouple 539, a closed circuit is formed by two different metal wires, and a heat electromotive force is generated corresponding to a temperature difference between the junctions of the metal wires, whereby thermoelectric power is flowed. In the first thermocouple 538 and the second thermocouple 539, the end portion including one of the junctions (distal end portions 538a and 539a) is exposed to the outside, and when mucosa and the like contacts the exposed junction, the temperature of the junction is changed, whereby the electrical current value is changed.

An outer peripheral surface of the connecting portion 537 has a stepped shape along the longitudinal direction of the distal end portion 53b. The connecting portion 537 has a hole portion 537a that is a hole into which a part of the illumination fiber 501, the first light receiving fiber 511, the second light receiving fiber 512, and the third light receiving fiber 513 is inserted.

Figure 13:
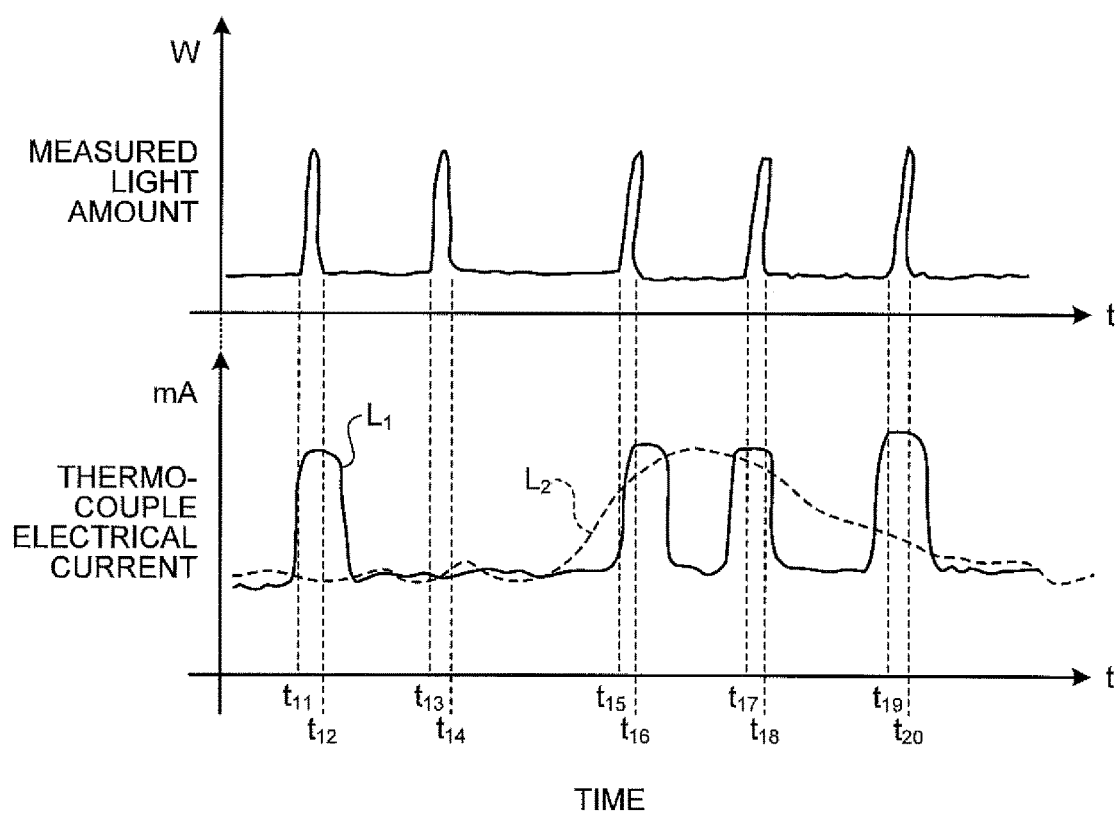
FIG. 13 is a graphical illustration of contact between the distal end portion of the measurement probe according to the third embodiment of the present invention and the living tissue, which is a graph showing a temporal change of a measured light amount and an electrical current value of a thermocouple.

FIG. 13 is a graphical illustration of the contact between the distal end portion of the measurement probe and living tissue according to the third embodiment of the present invention, which is a graph showing a time (t) change of a measured light amount (W) and an electrical current value (mA) of the thermocouple. In FIG. 13, a change of the electrical current value by the first thermocouple 538 is denoted by a curved line $L_1$, and a change of the electrical current value by the second thermocouple 539 is denoted by a curved line $L_2$. FIG. 13 provides an example of performing the measurement five times in total between a time $t_{11}$ and a time $t_{12}$, between a time $t_{13}$ and a time $t_{14}$, between a time $t_{15}$ and a time $t_{16}$, between a time $t_{17}$ and a time $t_{18}$, and between a time $t_{19}$ and a time $t_{20}$. Hereinafter, the measurement performed between the time $t_{11}$ and the time $t_{12}$ is referred to as a first measurement, the measurement performed between the time $t_{13}$ and the time $t_{14}$ is referred to as a second measurement, the measurement performed between the time $t_{15}$ and the time $t_{15}$ is referred to as a third measurement, the measurement performed between the time $t_{17}$ and the time $t_{18}$ is referred to as a fourth measurement, and the measurement performed between the time $t_{19}$ and the time $t_{20}$ is referred to as a fifth measurement.

In the first measurement, the measured light amount and the electrical current value by the first thermocouple 538 increases while the amount of change of the electrical current value by the second thermocouple 539 is small. In a case where the measurement is performed in the ideal contact state between the measurement probe 5 and the living tissue 200, the distal end portion 538a of the first thermocouple 538 contacts the mucosa, the villus 202, and the like of the living tissue 200. In contrast, the distal end portion 539a of the second thermocouple 539 does not contact the mucosa, the villus 202, and the like of the living tissue 200. For this reason, in a case where it is in an ideal contact, the electrical current value by the first thermocouple 538 largely changes while the electrical current value by the second thermocouple 539 hardly changes. Therefore, the first measurement may be regarded as being measured in the ideal contact state between the measurement probe 5 and the living tissue 200.

In the second measurement, the measured light amount increases while the amounts of change of the electrical current values by the first thermocouple 538 and the second thermocouple 539 are small. In a case where there is no change of the electrical current values by the first thermocouple 538, it is assumed that the measurement probe 5 and the living tissue 200 are not in contact. Therefore, the second measurement may be regarded as being measured in the non-ideal contact state between the measurement probe 5 and the living tissue 200.

In the third and the fourth measurements, the measured light amount as well as each of the electrical current values by the first thermocouple 538 and the second thermocouple 539 increases. In a case where the electrical current value of the second thermocouple 539 increases, it is assumed that a side surface of the measurement probe 5, which is a side surface including at least the distal end portion 539a of the second thermocouple 539, is in contact with the living tissue 200, and the distal end of the measurement probe 5 is sinking into the living tissue 200. Therefore, the third and the fourth measurements may be regarded as being measured in the non-ideal contact state between the measurement probe 5 and the living tissue 200.

In the fifth measurement, the measured light amount as well as each of the electrical current values by the first thermocouple 538 and the second thermocouple 539 increases. The electrical current value by the second thermocouple 539 is small compared to the electrical current value by the third and the fourth measurements, and it is slightly large compared to the electrical current value of the first measurement. The electrical current value of the fifth measurement is detected while temporally descending from the time of the fourth measurement, and in this case, the side surface of the measurement probe 5, which is the side surface including at least the distal end portion 539a of the second thermocouple 539, is not in contact with the living tissue 200, whereby it is assumed that the electrical current value is high compared to the first measurement due to a transient property of the second thermocouple 539. Therefore, the fifth measurement may be regarded as being measured in the ideal contact state between the measurement probe 5 and the living tissue 200.

As described above, in the ideal contact state between the measurement probe 5 and the living tissue 200, a change of the detection value (electrical current value) detected through the distal end portion 53b is small, and in the non-ideal contact state between the measurement probe 5 and the living tissue 200, the change of the detection value (electrical current value) detected through the distal end portion 53b is large. By comparing this change of the electrical current value with a threshold, the detecting unit 24 determines the contact state between the measurement probe 5 and the living tissue 200. Specifically, the detecting unit 24 compares the detection value with the threshold, for example, by using any of a maximum value, a minimum value, an average value, and a most frequent value of the electrical current value detected between the time $t_1$ and the time $t_2$ in the first measurement as the detection value. In a case where the detection value is larger than the threshold, it is determined that the first measurement is performed in the non-ideal contact state between the measurement probe 5 and the living tissue 200. That is, by determining that the measurement is performed in the non-ideal contact state between the measurement probe 5 and the living tissue 200, the detecting unit 24 detects whether or not the distal end of the measurement probe 5 is sunk in the living tissue 200. The detecting unit 24 determines the contact state based on the detection value detected in the same way during each measurement period.

As in the fifth measurement, although the side surface of the measurement probe 5, which is the side surface including at least the distal end portion 539a of the second thermocouple 539, and the living tissue 200 are not in contact, the electrical current value may become high compared to the first measurement due to the transient property of the second thermocouple 539. Considering such properties, it is preferred that a threshold for determining the ideal and non-ideal contact states for the electrical current value of the second thermocouple 539 be set. It is preferred that whether or not the distal end portion 539a of the second thermocouple 539 is in contact with the living tissue 200 be determined by comparing the threshold with the electrical current value. The threshold may be an electrical current value set according to the transient property or may be a value increased by several percentages to several tens of percentages from an electrical current value when in the ideal contact state (for example, in the first measurement).

Subsequently, as in the above-described first embodiment, according to a detection result by the detecting unit 24, the control unit 26 may add information related to a contact state to the characteristic value related to the characteristics of the measuring object, or may display information related to the detected contact state on the display unit 3. Accordingly, it is possible to grasp whether the measurement has been performed in the ideal contact state, that is, in the contact state in which a highly-reliable measurement result can be obtained, or in the non-ideal contact state.

According to the above-described third embodiment of the present invention, in the distal end portion 53b of the measurement probe 5, based on the change of the electrical current value by the first thermocouple 538, which is provided at the distal end side where the measurement probe 5 is in contact with the measuring object, and the change of the electrical current value by the second thermocouple 539, which is provided at the position slightly apart from the distal end, detection of the sinking into the measuring object becomes possible by using the characteristics of the detection value that is different between when the measurement probe 5 is sinking into the measuring object and when the measurement probe 5 is not sinking into the measuring object. Accordingly, it is possible to determine reliability of the measurement result that has been obtained from the presence or the absence of the detection result, whereby it is possible to obtain an appropriate measurement result in the measurement performed by contacting the measurement probe to the living tissue.

In the above-described third embodiment, two thermocouples (the first thermocouple 538 and the second thermocouple 539) are used; however, detection of sinking is possible as long as at least the second thermocouple 539 is provided. That is, as long as the thermocouple is provided on the side portion of the measurement probe 5, it is possible to detect the sinking, and in order to securely detect the contact between the contact surface of the measurement probe 5 (rod lens 54) and the living tissue 200 as well, it is preferred that the first thermocouple 538 and the second thermocouple 539 be provided.

According to some embodiments, it is possible to obtain appropriate measurement results when performing the measurement by contacting a measurement probe with living tissue.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A measurement probe comprising:
a plurality of optical fibers including an illumination fiber configured to propagate light to irradiate a measuring object and including a light receiving fiber configured to receive scattered light retuned from the measuring object; and
a detection portion configured to detect contact with the measuring object, the detection portion having a contact part provided on a part of a side portion of the measurement probe, the side portion forming a surface along a longitudinal direction of the measurement probe, the contact part being configured to be in contact with measuring object.

2. The measurement probe according to claim 1, wherein the contact part is located away from an end portion of the measurement probe where the measurement probe is configured to be in contact with the measuring object, by a predetermined distance.

3. The measurement probe according to claim 1, wherein at least a part of the detection portion is exposed to outside to provide a pair of electrodes that is electrically connectable through the measuring object.

4. The measurement probe according to claim 1, wherein the detection portion includes a thermocouple having two different metallic members and two junctions connecting the metallic members, wherein
one of the two junctions is exposed to outside at the part of the side portion of the measurement probe.

5. The measurement probe according to claim 4, further comprising a second detection portion configured to detect contact with the measuring object, the second detection portion having a second contact part that is provided on a part of an end portion of the measurement probe in the longitudinal direction and that is configured to be in contact with the measuring object.

6. An optical measurement system comprising:
an optical measurement apparatus configured to perform an optical measurement on a measuring object to measure characteristics of the measuring object; and
a measurement probe having a plurality of optical fibers including an illumination fiber configured to propagate light to irradiate the measuring object and including a light receiving fiber configured to receive scattered light returned from the measuring object, wherein
the measurement probe comprises a detection portion configured to detect contact with the measuring object, the detection portion having a contact part provided on a part of a side portion of the measurement probe, the side portion forming a surface along a longitudinal direction of the measurement probe, the contact part being configured to be in contact with measuring object, and
the optical measurement apparatus comprises a detecting unit configured to detect whether or not the side portion on a distal end side of the measurement probe is being covered with the measuring object based on a detection value detected by the detection portion.

7. The optical measurement system according to claim 6, further comprising a storage unit configured to store information for detecting a contact state between the measurement probe and the measuring object, wherein
the detecting unit is configured to detect the contact state between the measurement probe and the measuring object based on the detection value and the information stored in the storage unit.

8. The optical measurement system according to claim 6, further comprising a display unit configured to display information on the characteristics of the measuring object measured based on a light reception result by the measurement probe as well as a detection result by the detecting unit regarding the contact state between the measurement probe and the measuring object.

9. The optical measurement system according to claim 6, further comprising a notifying unit configured to notify of a detection result by the detecting unit regarding the contact state between the measurement probe and the measuring object.

* * * * *